US00PP21005P2

(12) United States Plant Patent
Dozier, Jr. et al.

(10) Patent No.: US PP21,005 P2
(45) Date of Patent: May 25, 2010

(54) KIWI PLANT NAMED 'AU FITZGERALD'

(50) Latin Name: *Actinidia deliciosa A. Chev.*
Varietal Denomination: AU Fitzgerald

(75) Inventors: W. Alfred Dozier, Jr., Opelika, AL (US); Floyd M. Woods, Auburn, AL (US); Curtis J. Hansen, Opelika, AL (US); Jim Pitts, Clanton, AL (US); Robert C. Ebel, Immokalee, FL (US); Grace Montgomery Fitzgerald, Summerdale, AL (US); John P. Fitzgerald, legal representative, Summerdale, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/150,769

(22) Filed: Apr. 30, 2008

(51) Int. Cl.
*A01H 5/00* (2006.01)

(52) U.S. Cl. ..... Plt./156

(58) Field of Classification Search ..... Plt./156
See application file for complete search history.

*Primary Examiner*—June Hwu
(74) *Attorney, Agent, or Firm*—Haverstock & Owens LLP

(57) ABSTRACT

A new and distinct cultivar of the species *Actinidia deliciosa* A. Chev. is described. The parentage of this new cultivar is unknown, but it is most likely an open pollinated 'Haywood' as it was grown from seed collected from fruit purchased in a grocery store. The new cultivar is distinguished by a lower chilling requirement and higher yields, smaller fruit with a greater length times diameter ratio, and the fruit has a lower pH and higher titratable acidity, % soluble solids, % dry matter, reducing and total sugars, total and reduced form of ascorbic acid (Vitamin C), Vitamin C antioxidant capacity and cellular capacity to reduce free radicals is higher, lower levels of β-carotene, higher chlorophyll levels (a and b), lower phenolic content and higher flavonoid content than the comparison cultivar 'Hayward' in Alabama.

3 Drawing Sheets

RELATED APPLICATIONS

U.S. patent application Ser. No. 12/150,857, filed on April 30, 2008, and entitled "Kiwi plant named 'AU Authur'" is incorporated by reference herein.

Latin name of the genus and species of the plant claimed: *Actinidia deliciosa* A. Chev.

Variety denomination: 'AU FITZGERALD'.

BACKGROUND OF THE INVENTION

'Hayward' is the most commercialized female kiwi cultivar grown and marketed in the world. The 'Hayward' cultivar is produced commercially in California in the U.S. and in New Zealand, and is the kiwi fruit most often found in U.S. grocery stores. Attributes of the 'Hayward' cultivar that have led to its dominance of the kiwi market in the past are its distinctive green flesh, good flavor and long storage life. It is not known what male cultivar was used to pollinate the female flowers that produced the fruit and seed that resulted in the new cultivar. 'Matua' and 'Tomuri' are two male cultivars frequently used.

Both the 'Hayward' cultivar and the present invention are deciduous vines of *Actinidia deliciosa* A. Chev. The *Actinidia deliciosa* species originated in China and parts of Asia and is known as the Chinese gooseberry. Plant material of this species was taken to New Zealand where new cultivars such as 'Hayward' were developed. Due to the appearance of the fruit of the Chinese gooseberry, it was given the name kiwi fruit in New Zealand after the native kiwi bird.

Many plantings of the 'Hayward' cultivar were established in Alabama as well as the adjoining southeastern states. These plantings were established near the coast in most cases. The vines grew vigorously but were unfruitful. In Alabama, research plantings were established in different locations that varied from the coast to the center of the state. The location that the kiwi have been most productive is in the center of the state in Chilton County where the commercial peach industry is located. The 'Hayward' cultivar has not been productive there.

Research has shown that the 'Hayward' cultivar requires at least 900 hours of chilling for sufficient vegetative budbreak and flower development and that 1150 hours chilling is required for maximum flowering. From chilling requirement research, flower abortion decreased as chilling hours received increased for all cultivars.

SUMMARY OF THE INVENTION

Mrs. A. A. Fitzgerald of Summerdale, Ala. purchased kiwi fruit from a local grocery store and planted some seeds from the fruit. She ended up with one female and one male plant that bloomed together, were very productive and matured a crop of quality fruit. The fruit purchased was probably from the 'Hayward' cultivar.

The present invention relates to a new and distinctive kiwi cultivar having a generally cylindrical shaped fruit that has brown skin covered with medium length brown hairs that strongly adhere to the skin surface. The pericarp of the fruit is green.

In the climate of central Alabama, vegetative bud break occurs during the last two weeks of March and the bloom period occurs during the last week of April and the first two weeks of May, depending on the climate during the season. The fruit reaches a minimum percent soluble solids level of 6.5 in central Alabama by mid-October.

The seed from which 'AU Fitzgerald' originated from was originally planted at Summerdale, Ala., near the Gulf Coast in Baldwin County. It was very fruitful at its original location indicating it has a lower chilling requirement than the 'Hayward'. 'AU Fitzgerald'retained a statistically greater number of flowers than 'Hayward' at 700, 800 and 1000 chilling hours received. The data indicates that 'AU Fitzgerald' has a lower chilling requirement than 'Hayward', which explains the greater fruit set and yield of 'AU Fitzgerald' compared to 'Hayward' in Alabama.

DETAILED BOTANICAL DESCRIPTION

Figure 1:
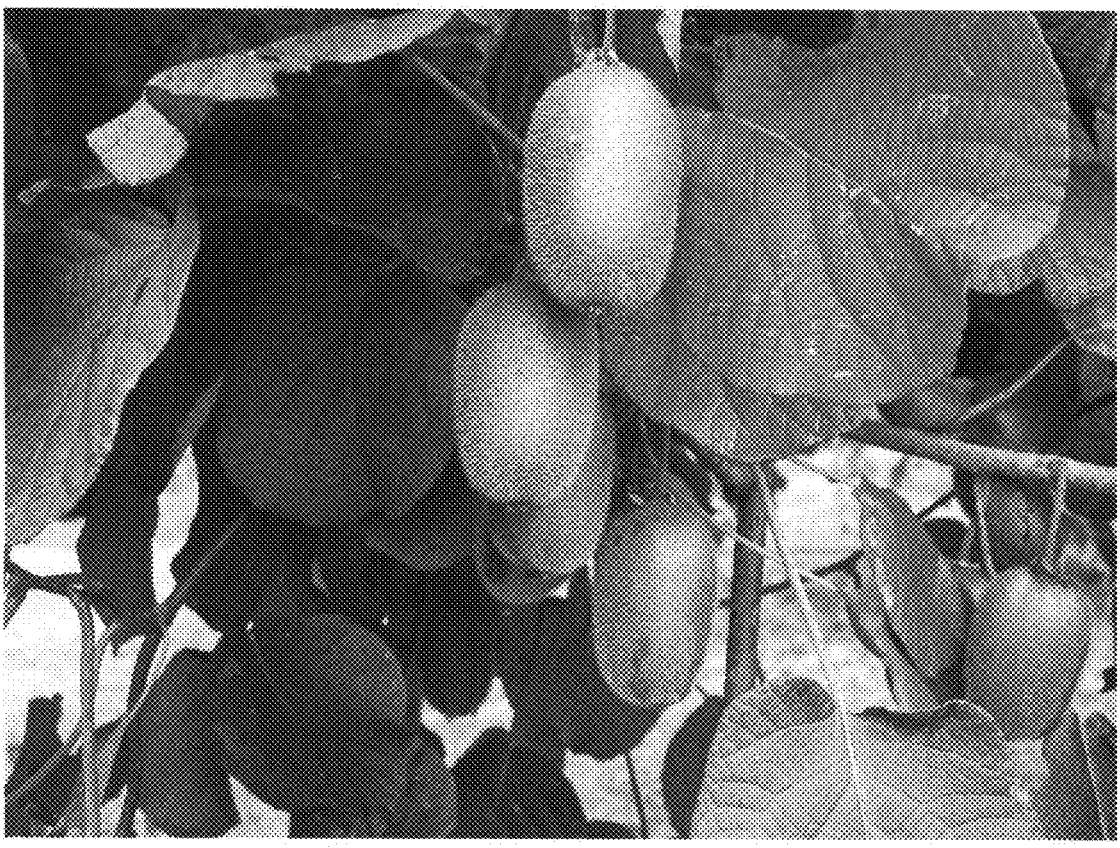
FIG. 1 is a photograph of hanging fruit of the 'AU Fitzgerald' cultivar.
Figure 2:
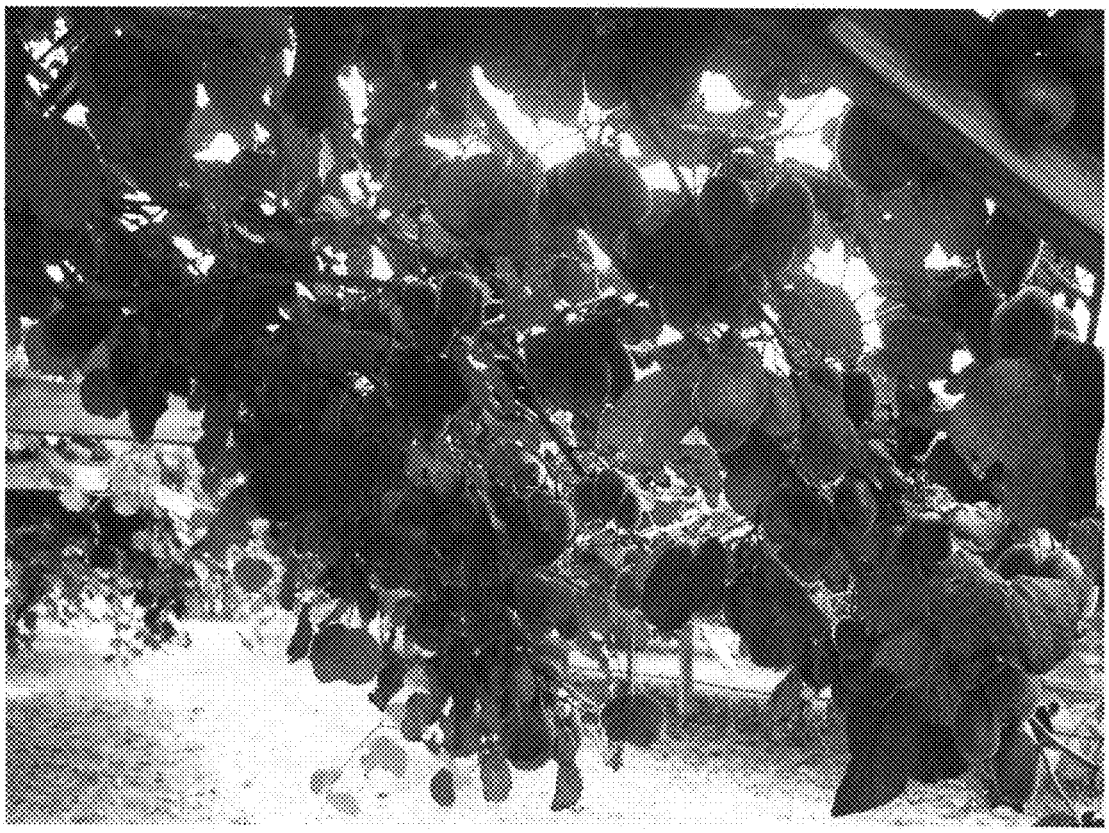
FIG. 2 is a photograph of vines with fruit of the 'AU Fitzgerald' cultivar.
Figure 3:
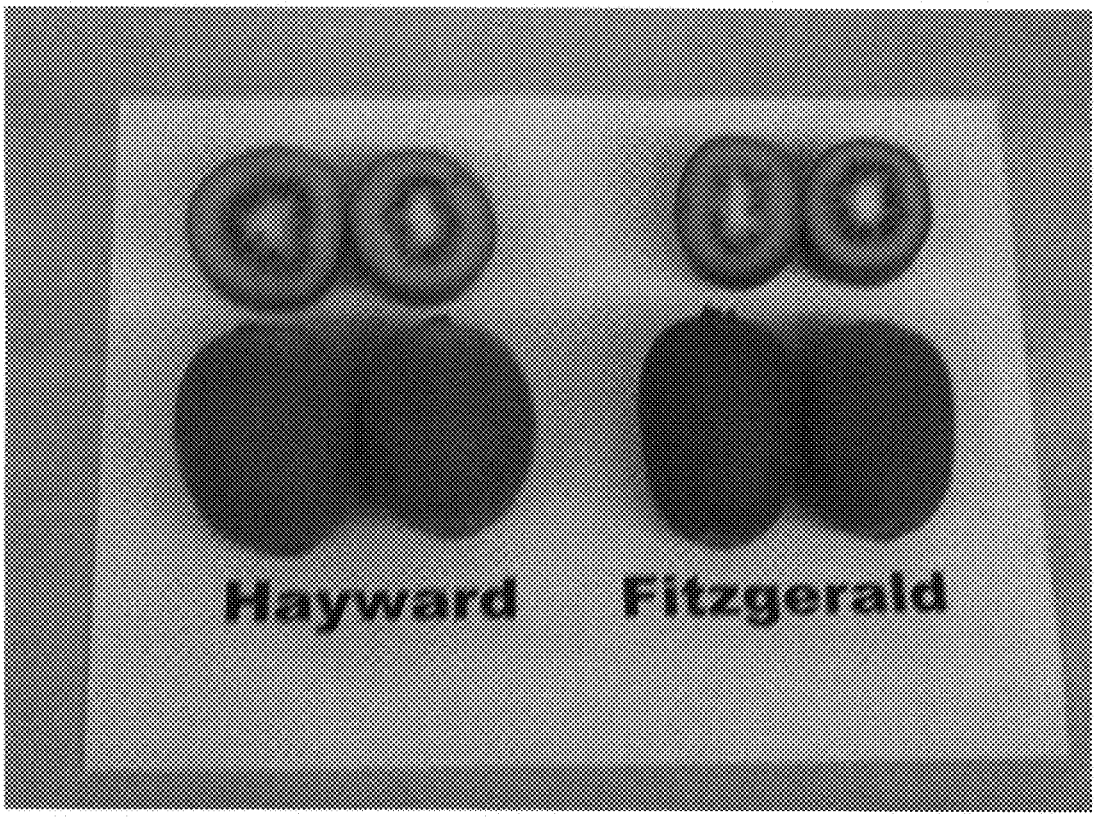
FIG. 3 is a photograph of fruit of the 'AU Fitzgerald' cultivar and the 'Hayward' cultivar.

The new cultivar 'AU Fitzgerald' is pistillate, with imperfect flowers, e.g. the flowers produce only sterile pollen and thus require a pollinizer for fruit production. Two *A. deliciosa* pollinizers, 'Matua' and 'AU Authur' have been used to pollinize 'AU Fitzgerald'.

The new cultivar is able to be asexually reproduced by softwood and hardwood cuttings or by grafting or budding on to a seedling or cutting grown rootstock. The new cultivar was asexually reproduced at the Chilton Area Research and Extension Center at Clanton, Ala., US. The instant plant was grafted on a rootstock named Bruno. The unique characteristics come true to form and are established and transmitted through succeeding asexual propagations.

The distinctive characteristics of this new kiwi cultivar described in detail below have been observed in a replicated field experiment at the Chilton Area Research and Extension Center at Clanton, Ala., US. The plants were one year old rooted cuttings when planted. The 'Hayward' cultivar was evaluated in the same replicated field experiment and was used as the standard cultivar for comparison.

Both the 'AU Fitzgerald' and 'Hayward' have a fruit shape in cross section that is generally cylindrical. However, the 'AU Fitzgerald' fruit is oblong to slightly ovate, whereas the 'Hayward' fruit is more broad elliptic to oblong. 'AU Fitzgerald' has a greater fruit length to diameter ratio. The shoulder on the stalk end of the fruit of each cultivar is rounded and flat and the stylar end of the fruit is flat and flush. The cultivars do not differ in flesh or skin color as measured by the Minolta calorimeter and The Royal Horticulture Society's Colour Chart (2001); however, higher chlorophyll a and b content were measured in 'AU Fitzgerald' and higher β-carotene content was measured in 'Hayward'.

'AU Fitzgerald' has a lower chilling requirement, smaller fruit size, greater fruit length to diameter ratio, greater fruit set and crop load, and the fruit has a lower pH and higher titratable acidity, % soluble solids, % dry matter, reducing and total sugars, total and reduced form of ascorbic acid (Vitamin C), Vitamin C antioxidant capacity and cellular capacity to reduce free radicals is higher, lower levels of β-carotene, higher chlorophyll levels (a and b), lower phenolic content and higher flavonoid content than the comparison cultivar 'Hayward' in Alabama.

The table below illustrates the specific differences between the 'AU Fitzgerald' cultivar and the 'Hayward' cultivar.

TABLE I

Comparison of 'AU Fitzgerald' and 'Hayward' cultivars.

| | 'AU Fitzgerald' | 'Hayward' |
|---|---|---|
| Plant | | |
| Plant: sex expression | female (flowers imperfect) | |
| Plant: ploidy | hexaploid | |
| Plant: vigor | medium | |
| Young shoot: hairs | present | |
| Young shoot: density of hairs | medium | |
| Young shoot: type of hairs | short | hirsute |
| Young shoot: anthocyanin coloration of growing tip | medium | |
| Young shoot: anthocyanin coloration of leaf axil | absent | |
| Plant: average height and spread | plant is a vine trained to grow on a trellis system. In the T-bar system rows are spaced 16 feet apart and plants are planted 8 feet apart in the row. The trellis is 6 feet wide. The vines are very vigorous and will cover the trellis by the end of the second year. To maintain and control the plant, the vines are pruned in the dormant season and several times during the growing season. | |
| Stem | | |
| Stem: coloration of leaf axil | weak | |
| Stem: diameter | medium | |
| Stem base diameter | mean 16.7 mm (range 15.6-18.7 mm) | mean 14.8 mm (range 14.6-15.1 mm) |
| Stem mid section diameter | mean 11.5 mm (range 11.3-11.8 mm) | mean 10.4 mm (range 9.3-11.6 mm) |
| Stem: dormant bud diameter | 7.4 mm (6.4-9.2 mm) | 7.71 mm (7.1-9.1 mm) |
| Stem: color on upper side of shoot | dark brown (N199B) | dark brown (200B) |
| Stem: character of bark | smooth | |
| Stem: hairs | present | |
| Stem: conspicuousness of lenticels | conspicuous | |
| Stem: number of lenticels | medium (258/sq cm) range (200-323/sq cm) | medium (239/sq cm) range (181-329/sq cm) |
| Stem: color of lenticels | brownish-white | |
| Stem: size of bud support | medium | |
| Stem: visibility of bud (dormant canes) | almost buried | |
| Stem: number of hairs visible on bud (dormant canes) | medium | |
| Stem: leaf scar | length (mm) - 4.8 (range 3.8-5.4) width (mm) - 4.3 (range 3.7-5.8) | |

TABLE I-continued

Comparison of 'AU Fitzgerald' and 'Hayward' cultivars.

| | 'AU Fitzgerald' | 'Hayward' |
|---|---|---|
| Leaf (Mature) | | |
| Leaf shape: | orbicular to broadly cordate | orbicular to reniforme |
| Leaf base shape: | rounded to somewhat cordate, lobes small and touching to slightly overlapping | cordate, lobes small and touching to slightly overlapping |
| Leaf tip shape: | round and shallowly cuspidate at tip | rounded, rarely refuse with broad cuspidate at tip |
| Leaf margin: | entire | |
| Leaf adaxial surface: | light-med green (147A), glabrous except for sparse, unbranched hairs on veins | |
| Leaf abaxial surface: | light green (148A), dense, stellate pubescence everywhere except along main veins which are densely tomentose with unbranched hairs | light green (147B); dense, stellate pubescence everywhere except along main veins which are densely tomentose with unbranched hairs |
| Leaf length (cm): | 17(15.4-19.3)[15] | 17.1(15.1-21.5)[15] |
| Leaf width (cm): | 14(12.8-15.5)[15] | 14.3(13.0-17.3)[15] |
| Leaf ratio (l/w): | 1.2(1.1-1.4)[15] | 1.2(1.0-1.7)[15] |
| Leaf petiole length (cm): | 4.9(4.3-5.6)[15] | 4.7(3.8-5.8)[15] |
| Leaf 1° vein organization: | pinnate; veins terminating as small extended points or mucros at leaf margins | |
| Leaf 2° vein organization: | ± parallel | |
| Leaf puckering: | moderate | weak |
| Leaf variegation: | none | |
| Leaf spines on lower leaf surface: | none | |
| Petiole: | 200B | |
| Peduncle: | 149B | |
| Flower | | |
| Inflorescence#: | mean 1.8 (range 1-3) [23] | mean 1.0 (range 1-1) [17] |
| 1° Pedicel length (cm): | 4.9(3.8-6.0)[13] | 5.0(3.8-5.8)[16] |
| 2° Pedicel length (cm): | 2.4(1.8-3.2)[13] | n/a |
| Pedicel pubescence: | minutely, densely tomentose, unbranched | |
| Sepal#: | 6.4(4-10)[10] | 6.3(5-8)[15] |
| Sepal color: | 152D | greenish-tan |
| Sepal pubescence: | minutely, densely tomentose, unbranched | |
| Flower color: | 10D | |
| Flower width (cm): | 6.4(5.3-7.5)[17] | 5.6(4.8-6.0)[13] |
| Petal orientation: | overlapping: sides reflexed | |
| Petal#: | 6.7(5-10) [23] | 7.3 (6-9) [14] |
| Petal length (cm): | 2.8(2.2-3.3)[20] | 2.6(2.3-3.1)[20] |
| Petal width (cm): | 2.4(1.8-2.9)[20] | 2.0(1.5-2.7)[20] |
| Petal ratio (l/w): | 1.2(1.0-1.4)[20] | 1.3(1.1-1.8)[20] |
| Petal arrangement: | overlapping | |
| Ovary shape: | globose to oblong | globose |
| Ovary pubescence: | strongly expressed (minutely, densely pilose, unbranched) | |
| Style#: | Average 32 Range 29-36 | >20 |
| Style orientation: | upright to spreading | |

TABLE I-continued

Comparison of 'AU Fitzgerald' and 'Hayward' cultivars.

| | 'AU Fitzgerald' | 'Hayward' |
|---|---|---|
| Stamen#: | Average 170 Range 160-190 | >40 |
| Anther length (mm): | 2.5-3.5 | 2.0-3.0 |
| Chilling requirement hours: | <800 | 1150 |
| Filament: | 10C | |
| Anther: | 21B | |
| Style: | 10C | |
| Fruit | | |
| Fruit: average size (g) | 60.2 (50.4-75.0) | 77.9 (64.1-89.7) |
| Fruit: length (mm) | 64.3 (57.0-69.8) | 63.3 (61.0-65.2) |
| Fruit: width (max) (mm) | 43.7 (40.7-46.5) | 49.0 47.1-50.8 |
| Fruit: L/A ratio (max width) | 1.46 | 1.29 |
| Fruit: width (min) (mm) | 38.5 34.9-41.3 | 44.8 42.6-46.2 |
| Fruit: L/D ratio (min width) | 1.68 | 1.42 |
| Fruit: core diameter (max) (mm) | 13.9 (5.0-24.3) | 12.4 (7.5-14.9) |
| Fruit: core diameter (min) (mm) | 6.7 (3.3-15.0) | 9.9 (4.6-18.8) |
| Fruit: locule number | 37.9 (31-51) | 38.4 (31-46) |
| Fruit: peduncle length (mm) | 59.6 50.7-64.7 | 46.88 38.6-55.9 |
| Fruit: peduncle width (mm) | 2.3 (1.7-2.7) | 2.8 (2.3-3.2) |
| Fruit: general shape | cylindrical, ovate | cylindrical, oblong |
| Fruit: cross-section at median | round | |
| Fruit: general shape of stylar end | flat, flush | |
| Fruit: skin color at harvest | 199A | |
| Fruit: skin color change during ripening | absent | |
| Fruit: skin color at maturity for consumption | brown | |
| Fruit: hairs | present | |
| Fruit: density of hairs | medium | |
| Fruit: types of hairs | hirsute | |
| Fruit: hair length (mm) | medium (1.1-2.5) | |
| Fruit: concentration of hairs | uniform | |
| Fruit: adherence of hairs to skin (when rubbed) | strong | |
| Fruit: core diameter (at largest diameter) | large (14.5 mm by 7.0 mm) | |
| Fruit: core shape (in cross section) | elliptical | |
| Fruit: core woody spike | present | |
| Fruit: prominence of core woody spike | medium | |
| Fruit: outer pericarp color at maturity for consumption | 147B | |
| Fruit: inner pericarp color (locules) at maturity for consumption | 148B | |
| Fruit: core color at maturity | 147D | |
| Fruit: seed color at maturity in flesh | 202A | |
| Fruit: seed color when dry | N199D | |

TABLE I-continued

Comparison of 'AU Fitzgerald' and 'Hayward' cultivars.

| | 'AU Fitzgerald' | 'Hayward' |
|---|---|---|
| Physiochemical and Antioxidant Characteristics at Harvest | | |
| pH | 3.83 | 3.89 |
| % Titratable Acidity (TA) | 0.61 | 0.49 |
| % Soluble Solid (SS) | 7.40 | 5.90 |
| Sugar/Acid Ratio (SS/TA) | 12.10 | 12.30 |
| Firmness (kg) | 6.05 | 6.27 |
| % dry matter | 20.10 | 17.30 |
| Sugar (mg/g.fw) | | |
| Reducing sugar | 25.87 | 16.01 |
| Non-reducing sugar | 11.59 | 18.63 |
| Total sugar | 37.46 | 34.64 |
| Vitamin C (mg/100 g.fw) | | |
| Total ascorbic acid | 74.49 | 70.13 |
| Ascorbic acid | 67.10 | 61.15 |
| Dehydroascorbic acid | 7.39 | 8.98 |
| TAA ratio % Hayward | 1.06 | 1.00 |
| AA ratio to TAA | 0.90 | 0.82 |
| Antioxidant | | |
| Vitamin C equivalent antioxidant capacity (VCEAC) (mg/100 g.fw) | 92.00 | 68.50 |
| Total Vit C/Total anti-oxidant ratio (%) - X | 0.81 | 1.02 |
| DPPH (mg/100 g.fw) | 168.90 | 129.60 |
| β-carotene (mg/100 g.fw) | 0.38 | 0.42 |
| β-carotene ratio to Hayward | 0.90 | 1.00 |
| Chlorophyll a + b ratio to Hayward | 1.05 | 1.00 |
| Chlorophyll a (mg/100 g.fw) | 0.97 | 0.91 |

TABLE I-continued

Comparison of 'AU Fitzgerald' and 'Hayward' cultivars.

| | 'AU Fitzgerald' | 'Hayward' |
|---|---|---|
| Chlorophyll b (mg/100 g.fw) | 0.53 | 0.53 |
| Chlorophyll a + b (mg/100 g.fw) | 1.50 | 1.44 |
| Sensory Characteristics at Consumption Stage | | |
| % Soluble Solids (SS) | 16.40 | 14.10 |
| % Dry matter | 19.05 | 17.30 |
| Firmness(kg) | <0.12 | <0.12 |
| Total Phenolics and Total Flavonoids at Consumption Stage | | |
| Total phenolics (mg GAE/100 g.fw) | 88.50 | 94.20 |
| Total flavonoids (mg CE/100 g.fw) | 28.90 | 27.00 |

Notes regarding Table I:

1. Horticulture terminology is used in accordance with revised UPOV guidelines for kiwi.

2. Characters of comparison cultivar 'Hayward' are noted opposite that character when significantly different.

3. 'Hayward' plants were observed in the same replicated study as the new cultivar.

4. All dimensions are in millimeters unless otherwise stated; weights are in grams.

What is claimed is:

1. A new and distinct variety of *Actinidia deliciosa* plant named 'AU Fitzgerald', substantially as described and illustrated herein.

* * * * *